(12) United States Patent
Graham et al.

(10) Patent No.: US 8,038,992 B2
(45) Date of Patent: Oct. 18, 2011

(54) TARGET FOR REGULATING MULTIPLE SCLEROSIS

(75) Inventors: Kareem Graham, Mountain View, CA (US); Brian A. Zabel, Mountain View, CA (US); Eugene C. Butcher, Portola Valley, CA (US)

(73) Assignees: The Board of Trustees of the Leland Stanford Junior University, Palo Alto, CA (US); Department of Veterans Affairs, Washington, DC (US)

( * ) Notice: Subject to any disclaimer, the term of this patent is extended or adjusted under 35 U.S.C. 154(b) by 346 days.

(21) Appl. No.: 12/463,840

(22) Filed: May 11, 2009

(65) Prior Publication Data

US 2009/0280113 A1    Nov. 12, 2009

Related U.S. Application Data

(60) Provisional application No. 61/052,189, filed on May 10, 2008.

(51) Int. Cl.
*A61K 39/395*    (2006.01)

(52) U.S. Cl. ............... 424/130.1; 424/133.1; 424/143.1; 424/144.1

(58) Field of Classification Search .................. None
See application file for complete search history.

(56) References Cited

OTHER PUBLICATIONS

Graham et al., Clinical Immunology, vol. 123 (Supplement 1), May 10, 2007, abstract No. OR.91, p. S138.*
Parolini et al., Blood, vol. 109, 2007, pp. 3625-3632.*
Cash et al., J. Experimental Medicine, vol. 205, Apr. 7, 2008, pp. 767-775.*

* cited by examiner

*Primary Examiner* — Zachariah Lucas
*Assistant Examiner* — Stephen Gucker
(74) *Attorney, Agent, or Firm* — Bozicevic, Field & Francis LLP; Pamela J. Sherwood

(57) ABSTRACT

Methods are provided for decreasing demyelinating inflammatory disease in a subject by inhibiting the activity of chemokine-like receptor 1 (CMKLR1). Methods are also provided for screening for agents that find use in treating demyelinating inflammatory disease in a subject.

2 Claims, 3 Drawing Sheets

TARGET FOR REGULATING MULTIPLE SCLEROSIS

FEDERALLY-SPONSORED RESEARCH OR DEVELOPMENT

This invention was made with Government support under contract AI059635 awarded by the National Institutes of Health. The Government has certain rights in this invention.

INTRODUCTION

Human chemokine-like receptor-1 (CMKLR1), a recently de-orphaned G-protein-coupled receptor (GPCR), is specifically expressed on in vitro monocyte-derived dendritic cells, ex vivo macrophages, and circulating plasmacytoid dendritic cells (pDCs) [Zabel, et al. J Immunol (2005) 174(1):244-51; Vermi, et al. J Exp Med (2005) 201(4):509-15]. The natural ligand for CMKLR1, chemerin, was recently discovered [Zabel, et al. J Immunol (2005) 174(1):244-51; Wittamer, V., et al., J Exp Med (2003) 198(7): 977-85; Meder, W., et al., FEBS Lett (2003) 555(3):495-9.]. Chemerin has been isolated from ascitic fluid (ovarian carcinoma), inflamed synovial fluid, hemofiltrate, and normal serum [Zabel, et al. J Immunol (2005) 174(1):244-51; Wittamer, V., et al., J Exp Med (2003) 198(7): 977-85; Meder, W., et al., FEBS Lett (2003) 555(3): 495-9.]. Chemerin, a heparin binding protein, initially exists in its pro-form, which is 163 amino acids long. Cleavage of pro-chemerin by serine proteases of inflammatory, coagulation, and fibrinolytic cascades results in the loss of the last 6-11 C-terminal amino acids. This proteolytic cleavage, which can be at a number of different sites in pro-chemerin, generates active chemerin and leads to a potent increase in ligand activity. This results in the increased migration of CMKLR1 bearing cells (e.g., macrophages) to chemerin [Wittamer, V., et al., J Immunol (2005) 175(1):487-93, Zabel, B. A., et al., J Biol Chem (2005) 280(41): 34661-6]. Chemerin thus acts as a macrophage and dendritic cell (DC) recruiting factor through its interaction with CMKLR1.

While CMKLR1 does not bind to chemokines, it has been reported that resolvin E1 (RvE1), a bioactive lipid generated upon aspirin-triggered enzymatic processing of omega-3 fatty acids, is a lipid ligand for CMKLR1 [Hasturk, et al. FASEB J. (2006) 20(2):401-3; Serhan Prostaglandins Leukot Essent Fatty Acids. (2005) 73(3-4):141-62].

Relevant Literature

The use of small molecules to block chemoattractant receptors is reviewed by Baggiolini and Moser (1997) J. Exp. Med. 186:1189-1191.

The sequence of chemerin (retinoic acid receptor responder 2 (RARRES2) II; tazarotene induced gene 2 product (TIG2)) may be found in Genbank, accession number NM_002889. The sequence of CMKLR1 may be found in Genbank, accession number Y14838, and is described by Samson et al. (1998) Eur J. Immunol. 28(5):1689-700. The sequence of a CMKLR1 ligand, mammalian chemerin, may be found in Genbank, accession number NM_002889.

SUMMARY OF THE INVENTION

The present invention is drawn to methods for decreasing demyelinating inflammatory disease in a subject by administering agents that decrease CMKLR1 activity. The therapeutic methods of the invention are useful for the treatment or prevention of MS and other diseases, e.g. experimental animal models such as experimental autoimmune encephalomyelitis (EAE). Inhibitors of CMKLR1 include, but are not limited to, agents that interfere with the interaction of CMKLR1 with its natural ligands, agents that reduce CMKLR1 expression (e.g., by reducing transcription or by inducing cell surface receptor desensitization and/or internalization), agents that reduce expression of endogenous ligands of CMKLR1, and agents that inhibit intracellular signals initiated by the binding of CMKLR1 with its ligands. Inhibitors include, without limitation, monoclonal antibodies, small molecules, chimeric proteins/peptides, bioactive peptides, and interfering RNA.

The present invention is also drawn to methods of screening for agents that can decrease demyelinating inflammatory disease when administered to a subject. In general, the screening method is designed to determine whether an agent can antagonize CMKLR1 activity in a cell. In certain embodiments, a cell expressing CMKLR1 (e.g., cells that normally express CMKLR1 or those that are genetically engineered to express CMKLR1) is contacted to a candidate agent and its response to a CMKLR1 ligand(s) is evaluated (e.g., chemotaxis, receptor/ligand binding, target gene expression, signaling responses, etc.). In certain other embodiments, a cell expressing CMKLR1 or a ligand is contacted to an agent and the expression level of CMKLR1 or its ligand is evaluated.

DESCRIPTION OF THE SPECIFIC EMBODIMENTS

Figure 1:
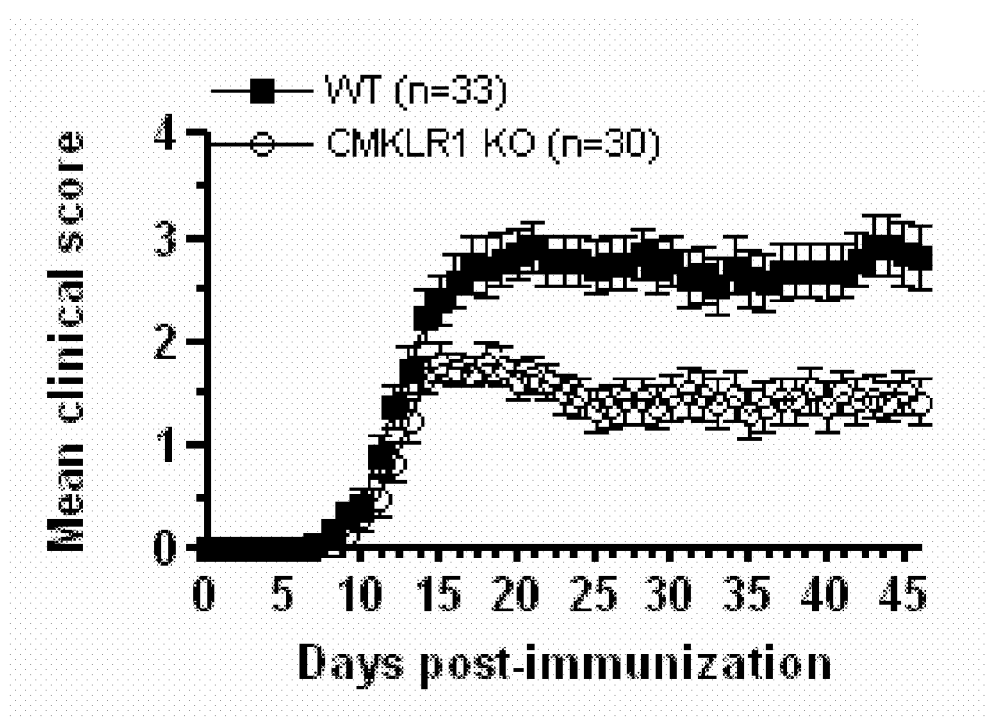
FIG. 1. Clinical EAE in CMKLR1 KO mice. EAE was induced by active immunization and mice were monitored daily for clinical disease. Data are pooled from five independent experiments and are presented as mean clinical ±s.e.m. versus time FIG. 2. Detection of CMKLR1$^+$ dendritic cells and microglia in the central nervous system (CNS) of mice with EAE. Mononuclear cells were isolated from the spinal cords of 3 mice with acute EAE and pooled for analysis. CD45$^{hi}$CD3$^-$CD19$^-$ cells were analyzed for expression of CD11b, CD11c, and B220. CD11c$^{hi}$CD11b$^+$B220$^-$ mDC expressed CMKLR1 while CD11c$^{int}$CD11b$^-$B220$^+$ pDC were CMKLR1-negative. CD3$^-$CD19$^-$CD11b$^+$CD45$^{lo}$ microglia expressed mCMKLR1. A representative data set of three independent experiments with similar results is shown.
Figure 2:
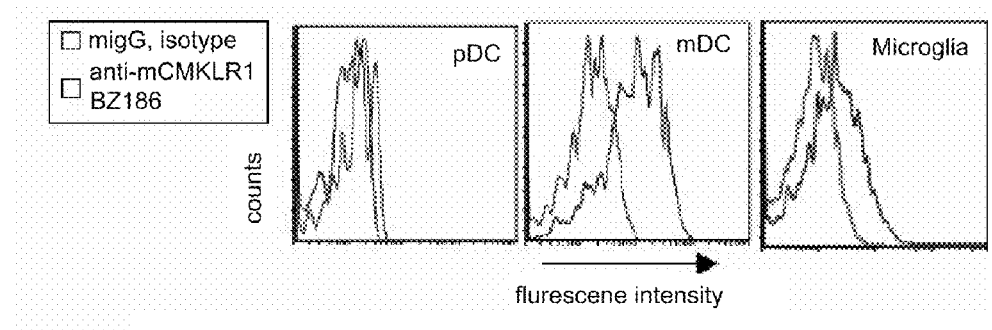
Figure 3:
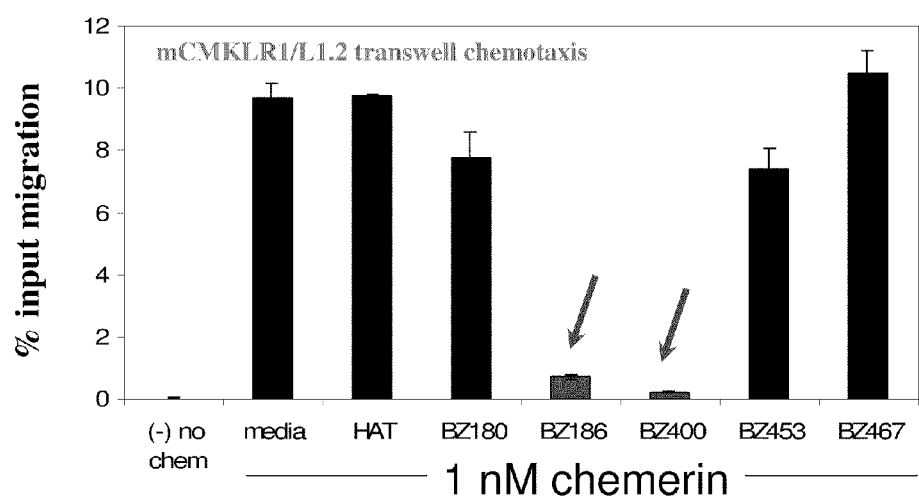
FIG. 3. anti-mCMKLR1 mAbs block chemerin-mediated chemotaxis in vitro.

As summarized above, the present invention is drawn to methods for treating demyelinating inflammatory disease in a subject by administering an agent that antagonizes the activity of chemokine-like receptor 1 (CMKLR1) and/or a CMKLR1 ligand (e.g., chemerin or other endogenous CMKLR1 ligands. As such, the methods of the invention find use in treating EAE or MS in a subject. Methods of screening for agents that regulate demyelinating inflammatory disease are also provided.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

"Activity" of CMKLR1 shall mean any signaling or binding function performed by that protein.

"Antibody" shall include, by way of example, both naturally occurring and non-naturally occurring antibodies. Specifically, this term includes polyclonal and monoclonal antibodies, and fragments thereof. Furthermore, this term includes chimeric antibodies and wholly synthetic antibodies, and fragments thereof. Monoclonal antibodies are provided that bind to CMKLR1 and block its activity. In some embodiments the antibody binds to the epitope that is bound by the monoclonal antibody BZ186. In other embodiments the monoclonal antibody binds to human counterpart of the epitope recognized by BZ186.

"Anti-sense nucleic acid" shall mean any nucleic acid which, when introduced into a cell, specifically hybridizes to at least a portion of an mRNA in the cell encoding a protein ("target protein") whose expression is to be inhibited, and thereby inhibits the target protein's expression.

"Comparable cell" shall mean a cell whose type is identical to that of another cell to which it is compared. Examples of comparable cells are cells from the same cell line.

"Expressible nucleic acid" shall mean a nucleic acid encoding a nucleic acid of interest and/or a protein of interest, which nucleic acid is an expression vector, plasmid or other construct which, when placed in a cell, permits the expression of the nucleic acid or protein of interest. Expression vectors and plasmids are well known in the art.

"Inhibiting" the onset of a disorder shall mean either lessening the likelihood of the disorder's onset, or preventing the onset of the disorder entirely. In the preferred embodiment, inhibiting the onset of a disorder means preventing its onset entirely. As used herein, onset may also refer to deterioration in a patient that has chronic/progressive disease, or relapse in a patient that has ongoing relapsing-remitting disease.

The methods of the invention may be specifically applied to individuals that have been diagnosed with an autoimmune disease, e.g. a chronic/progressive or relapsing-remitting disease such as MS or EAE. Treatment is aimed at the treatment or prevention of relapses, which are an exacerbation of a pre-existing condition.

"Inhibiting" the expression of a gene in a cell shall mean either lessening the degree to which the gene is expressed, or preventing such expression entirely.

"Nucleic acid" shall mean any nucleic acid molecule, including, without limitation, DNA, RNA and hybrids thereof. The nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996-1997, Roche Molecular Systems, Inc., Branchburg, N.J., USA).

Active fragments of CMKLR1 share a functional or binding property with full length CMKLR1.

Epitopic fragments of CMKLR1 bind to a monoclonal antibody that binds to full length CMKLR1, including native or denatured forms of the protein.

"Specifically hybridize" to a nucleic acid shall mean, with respect to a first nucleic acid, that the first nucleic acid hybridizes to a second nucleic acid with greater affinity than to any other nucleic acid.

"Specifically inhibit" the expression of a protein shall mean to inhibit that protein's expression or activity (a) more than the expression or activity of any other protein, or (b) more than the expression or activity of all but 10 or fewer other proteins.

"Subject" or "patient" shall mean any animal, such as a human, non-human primate, mouse, rat, guinea pig or rabbit.

"Suitable conditions" shall have a meaning dependent on the context in which this term is used. That is, when used in connection with an antibody, the term shall mean conditions that permit an antibody to bind to its corresponding antigen. When this term is used in connection with nucleic acid hybridization, the term shall mean conditions that permit a nucleic acid of at least 15 nucleotides in length to hybridize to a nucleic acid having a sequence complementary thereto. When used in connection with contacting an agent to a cell, this term shall mean conditions that permit an agent capable of doing so to enter a cell and perform its intended function. In one embodiment, the term "suitable conditions" as used herein means physiological conditions.

"Treating" a disorder shall mean slowing, stopping or reversing the disorder's progression. In the preferred embodiment, treating a disorder means reversing the disorder's progression, ideally to the point of eliminating the disorder itself. As used herein, ameliorating a disorder and treating a disorder are equivalent.

The term "immune" response is the development of a beneficial humoral (antibody mediated) and/or a cellular (mediated by antigen-specific T cells or their secretion products) response directed against CMKLR1 in a recipient patient. Such a response can be an active response induced by an "immunogen" that is capable of inducing an immunological response against itself on administration to a mammal, optionally in conjunction with an adjuvant.

Methods of the Invention

The present invention provides methods for treating autoimmune disease, including inflammatory demyelinating diseases, such multiple sclerosis; etc. These methods comprise administering to the subject having an autoimmune condition, e.g. a demyelinating condition; an effective amount of an inhibitor of CMKLR1.

In some embodiments, a method is provided for inhibiting autoimmune diseases in a subject, the method comprising administering to the subject a prophylactically effective amount of a nucleic acid that specifically reduces levels of CMKLR1, e.g. an anti-sense oligonucleotide, siRNA, and the like.

In other embodiments, a method is provided for inhibiting inflammatory demyelinating disease in a subject, the method comprising administering to the subject a therapeutically effective amount of an anti-CMKLR1 antibody or antigen-binding portion thereof.

In other embodiments, the method comprising administering to said subject an agent that downregulates the expression, or inhibits the activity of, a ligand of CMKLR1, which ligand includes, without limitation, chemerin. In these methods, the CMKLR1-expressing cell can be, without limitation, a macrophage; a dendritic cell; or a microglial cell.

This invention can utilize a method for reducing the amount of CMKLR1 in a CMKLR1-expressing cell comprising introducing into the cell a nucleic acid which specifically inhibits CMKLR1 expression in the cell. In one embodiment, this method further reduces the amount of CMKLR1 secreted by a CMKLR1-secreting cell. In this method, the nucleic acid can be, for example, DNA or RNA. In addition, the nucleic acid can be an anti-sense nucleic acid that hybridizes to CMKLR1-encoding mRNA, an siRNA that inhibits CMKLR1 expression, or a catalytic nucleic acid that cleaves CMKLR1-encoding mRNA. CMKLR1 expression can also be inhibited using zinc finger proteins or nucleic acids encoding the same as described in WO 00100409. Alternatively, inhibition of expression can be achieved using siRNAs as described by WO 99132619, Elbashir, EMBO J. 20, 6877-6888 (2001) and Nykanen et al., Cell 107, 309-321 (2001); WO 01129058.

The antisense reagent may be antisense oligonucleotides (ODN), particularly synthetic ODN having chemical modifications from native nucleic acids, or nucleic acid constructs that express such antisense molecules as RNA. The antisense sequence is complementary to the targeted miRNA, and inhibits its expression. One or a combination of antisense molecules may be administered, where a combination may comprise multiple different sequences.

Antisense molecules may be produced by expression of all or a part of the target miRNA sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 25, usually not more than about 23-22 nucleotides in length, where the length is governed by efficiency of inhibition, specificity, including absence of cross-reactivity, and the like.

Antisense oligonucleotides may be chemically synthesized by methods known in the art (see Wagner et al. (1993) supra. and Milligan et al., supra.) Preferred oligonucleotides are chemically modified from the native phosphodiester structure, in order to increase their intracellular stability and binding affinity. A number of such modifications have been described in the literature that alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The alpha.-anomer of deoxyribose may be used, where the base is inverted with respect to the natural beta.-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

Anti-sense molecules of interest include antagomir RNAs, e.g. as described by Krutzfeldt et al., supra., herein specifically incorporated by reference. Small interfering double-stranded RNAs (siRNAs) engineered with certain 'drug-like' properties such as chemical modifications for stability and cholesterol conjugation for delivery have been shown to achieve therapeutic silencing of an endogenous gene in vivo. To develop a pharmacological approach for silencing miRNAs in vivo, chemically modified, cholesterol-conjugated single-stranded RNA analogues complementary to miRNAs were developed, termed 'antagomirs'. Antagomir RNAs may be synthesized using standard solid phase oligonucleotide synthesis protocols. The RNAs are conjugated to cholesterol, and may further have a phosphorothioate backbone at one or more positions.

Also of interest in certain embodiments are RNAi agents. In representative embodiments, the RNAi agent targets the precursor molecule of the microRNA, known as pre-microRNA molecule. By RNAi agent is meant an agent that modulates expression of microRNA by a RNA interference mechanism. The RNAi agents employed in one embodiment of the subject invention are small ribonucleic acid molecules (also referred to herein as interfering ribonucleic acids), i.e., oligoribonucleotides, that are present in duplex structures, e.g., two distinct oligoribonucleotides hybridized to each other or a single ribooligonucleotide that assumes a small hairpin formation to produce a duplex structure. By oligoribonucleotide is meant a ribonucleic acid that does not exceed about 100 nt in length, and typically does not exceed about 75 nt length, where the length in certain embodiments is less than about 70 nt. Where the RNA agent is a duplex structure of two distinct ribonucleic acids hybridized to each other, e.g., an siRNA, the length of the duplex structure typically ranges from about 15 to 30 bp, usually from about 15 to 29 bp, where lengths between about 20 and 29 bps, e.g., 21 bp, 22 bp, are of particular interest in certain embodiments. Where the RNA agent is a duplex structure of a single ribonucleic acid that is present in a hairpin formation, i.e., a shRNA, the length of the hybridized portion of the hairpin is typically the same as that provided above for the siRNA type of agent or longer by 4-8 nucleotides. The weight of the RNAi agents of this embodiment typically ranges from about 5,000 daltons to about 35,000 daltons, and in many embodiments is at least about 10,000 daltons and less than about 27,500 daltons, often less than about 25,000 daltons.

dsRNA can be prepared according to any of a number of methods that are known in the art, including in vitro and in vivo methods, as well as by synthetic chemistry approaches. Examples of such methods include, but are not limited to, the methods described by Sadher et al. (Biochem. Int. 14:1015, 1987); by Bhattacharyya (Nature 343:484, 1990); and by Livache, et al. (U.S. Pat. No. 5,795,715), each of which is incorporated herein by reference in its entirety. Single-stranded RNA can also be produced using a combination of enzymatic and organic synthesis or by total organic synthesis. The use of synthetic chemical methods enable one to introduce desired modified nucleotides or nucleotide analogs into the dsRNA. dsRNA can also be prepared in vivo according to a number of established methods (see, e.g., Sambrook, et al. (1989) Molecular Cloning: A Laboratory Manual, 2nd ed.; Transcription and Translation (B. D. Hames, and S. J. Higgins, Eds., 1984); DNA Cloning, volumes 1 and 11 (D. N. Glover, Ed., 1985); and Oligonucleotide Synthesis (M. J. Gait, Ed., 1984, each of which is incorporated herein by reference in its entirety).

In certain embodiments, instead of the RNAi agent being an interfering ribonucleic acid, e.g., an siRNA or shRNA as described above, the RNAi agent may encode an interfering ribonucleic acid, e.g., an shRNA, as described above. In other words, the RNAi agent may be a transcriptional template of the interfering ribonucleic acid. In these embodiments, the transcriptional template is typically a DNA that encodes the interfering ribonucleic acid. The DNA may be present in a vector, where a variety of different vectors are known in the art, e.g., a plasmid vector, a viral vector, etc.

As indicated above, the antisense agent can be introduced into the target cell(s) using any convenient protocol, where the protocol will vary depending on whether the target cells are in vitro or in vivo. A number of options can be utilized to deliver the dsRNA into a cell or population of cells such as in a cell culture, tissue, organ or embryo. For instance, RNA can be directly introduced intracellularly. Various physical methods are generally utilized in such instances, such as administration by microinjection (see, e.g., Zernicka-Goetz, et al. (1997) Development 124:1133-1137; and Wianny, et al. (1998) Chromosoma 107: 430-439). Other options for cellular delivery include permeabilizing the cell membrane and electroporation in the presence of the dsRNA, liposome-mediated transfection, or transfection using chemicals such as calcium phosphate. A number of established gene therapy techniques can also be utilized to introduce the dsRNA into a cell. By introducing a viral construct within a viral particle, for instance, one can achieve efficient introduction of an expression construct into the cell and transcription of the RNA encoded by the construct.

For example, the inhibitory agent can be fed directly to, injected into, the host organism containing the target gene. The agent may be directly introduced into the cell (i.e., intracellularly); or introduced extracellularly into a cavity, interstitial space, into the circulation of an organism, introduced orally, etc. Methods for oral introduction include direct mixing of RNA with food of the organism. Physical methods of introducing nucleic acids include injection directly into the cell or extracellular injection into the organism of an RNA solution. The agent may be introduced in an amount which allows delivery of at least one copy per cell. Higher doses (e.g., at least 5, 10, 100, 500 or 1000 copies per cell) of the agent may yield more effective inhibition; lower doses may also be useful for specific applications.

When liposomes are utilized, substrates that bind to a cell-surface membrane protein associated with endocytosis can be attached to the liposome to target the liposome to macrophages or dendritic cells and to facilitate uptake. Examples of proteins that can be attached include capsid proteins or fragments thereof that bind to macrophages or dendritic cells, antibodies that specifically bind to cell-surface proteins on macrophages or dendritic cells that undergo internalization in cycling and proteins that target intracellular localizations within T cells. Gene marking and gene therapy protocols are reviewed by Anderson et al. (1992) Science 256:808-813.

In certain embodiments, a hydrodynamic nucleic acid administration protocol is employed. Where the agent is a ribonucleic acid, the hydrodynamic ribonucleic acid administration protocol described in detail below is of particular interest. Where the agent is a deoxyribonucleic acid, the hydrodynamic deoxyribonucleic acid administration protocols described in Chang et al., J. Virol. (2001) 75:3469-3473; Liu et al., Gene Ther. (1999) 6:1258-1266; Wolff et al., Science (1990) 247: 1465-1468; Zhang et al., Hum. Gene Ther. (1999) 10:1735-1737: and Zhang et al., Gene Ther. (1999) 7:1344-1349; are of interest.

Additional nucleic acid delivery protocols of interest include, but are not limited to: those described in U.S. patents of interest include U.S. Pat. Nos. 5,985,847 and 5,922,687 (the disclosures of which are herein incorporated by reference); WO/11092; Acsadi et al., New Biol. (1991) 3:71-81; Hickman et al., Hum. Gen. Ther. (1994) 5:1477-1483; and Wolff et al., Science (1990) 247: 1465-1468; etc.

In another embodiment, relapse of an autoimmune disease in a subject is inhibited or prevented by administering to the subject a prophylactically or therapeutically effective amount of an anti-CMKLR1 antibody or antigen-binding portion thereof.

Determining a therapeutically or prophylactically effective amount of the CMKLR1 inhibitor compositions can be done based on animal data using routine computational methods. In one embodiment, the therapeutically or prophylactically effective amount contains between about 0.1 mg and about 1 g of nucleic acid or protein, as applicable. In another embodiment, the effective amount contains between about 1 mg and about 100 mg of nucleic acid or protein, as applicable. In a further embodiment, the effective amount contains between about 10 mg and about 50 mg of the nucleic acid or protein, as applicable.

In this invention, administering the instant compositions can be effected or performed using any of the various methods and delivery systems known to those skilled in the art. The administering can be performed, for example, intravenously, orally, via implant, transmucosally, transdermally, intramuscularly, intrathecally, and subcutaneously. The following delivery systems, which employ a number of routinely used pharmaceutical carriers, are only representative of the many embodiments envisioned for administering the instant compositions.

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's). Implantable systems include rods and discs, and can contain excipients such as PLGA and polycaprylactone. CMKLR1 or nucleic acids of the invention can also be administered attached to particles using a gene gun.

Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

Solutions, suspensions and powders for reconstitutable delivery systems include vehicles such as suspending agents (e.g., gums, xanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and Jun. 2, 2005 antioxidants (e.g., parabens, vitamins E and C, and ascorbic acid), anti-caking agents, coating agents, and chelating agents (e.g., EDTA).

Conditions for Analysis and Therapy

The compositions and methods of the invention find use in combination with a variety of demyelinating autoimmune conditions, including chronic/progressive and relapsing demyelinating autoimmune diseases. Generally patients for the methods of the present invention are diagnosed as having an autoimmune condition, e.g. a relapsing-remitting autoimmune condition, prior to treatment. The inhibition of CMKLR1 decreases the severity or incidence of relapses in such patients.

Multiple sclerosis (MS) is characterized by various symptoms and signs of CNS dysfunction, with remissions and recurring exacerbations. The most common presenting symptoms are paresthesias in one or more extremities, in the trunk, or on one side of the face; weakness or clumsiness of a leg or hand; or visual disturbances, e.g. partial blindness and pain in one eye (retrobulbar optic neuritis), dimness of vision, or scotomas. Other common early symptoms are ocular palsy resulting in double vision (diplopia), transient weakness of one or more extremities, slight stiffness or unusual fatigability of a limb, minor gait disturbances, difficulty with bladder control, vertigo, and mild emotional disturbances; all indicate scattered CNS involvement and often occur months or years before the disease is recognized. Excess heat may accentuate symptoms and signs.

Clinical data alone may be sufficient for a diagnosis of MS. If an individual has suffered two separate episodes of neurologic symptoms characteristic of MS, and the individual also has consistent abnormalities on physical examination, a diagnosis of MS can be made with no further testing. Magnetic resonance imaging (MRI) of the brain and spine is often used during the diagnostic process. MRI shows areas of demyelination (lesions) as bright spots on the image. A substance, called Gadolinium, can be injected into the spinal column to highlight active plaques and, by elimination, demonstrate the existence of historical lesions not associated with clinical symptoms. This can provide the evidence of chronic disease needed for a definitive diagnosis of MS. Testing of cerebrospinal fluid (CSF) can provide evidence of chronic inflammation of the central nervous system. The CSF is tested for oligoclonal bands, which are immunoglobulins found in 85% to 95% of people with definite MS. Combined with MRI and clinical data, the presence of oligoclonal bands can help make a definite diagnosis of MS. Lumbar puncture is the procedure used to collect a sample of CSF.

The brain of a person with MS often responds less actively to stimulation of the optic nerve and sensory nerves. These brain responses can be examined using visual evoked potentials (VEPs) and somatosensory evoked potentials (SEPs). Decreased activity on either test can reveal demyelination which may be otherwise asymptomatic. Along with other data, these exams can help find the widespread nerve involvement required for a definite diagnosis of MS.

In 1996 the United States National Multiple Sclerosis Society standardized the following four subtype definitions (see Lublin and Reingold (1996) Neurology 46(4):907-11, herein specifically incorporated by reference) as relapsing-remitting; secondary progressive; primary progressive; progressive relapsing. The methods of the invention find particular use in the treatment of ongoing disease, and particularly in treating relapsing forms.

Relapsing-remitting describes the initial course of 85% to 90% of individuals with MS. This subtype is characterized by unpredictable attacks (relapses) followed by periods of months to years of relative quiet (remission) with no new signs of disease activity. Deficits suffered during the attacks may either resolve or may be permanent. When deficits always resolve between attacks, this is referred to as "benign" MS.

Secondary progressive describes around 80% of those with initial relapsing-remitting MS, who then begin to have neurologic decline between their acute attacks without any definite periods of remission. This decline may include new neurologic symptoms, worsening cognitive function, or other deficits. Secondary progressive is the most common type of MS and causes the greatest amount of disability.

Primary progressive describes the approximately 10% of individuals who never have remission after their initial MS symptoms. Decline occurs continuously without clear attacks. The primary progressive subtype tends to affect people who are older at disease onset.

Progressive relapsing describes those individuals who, from the onset of their MS, have a steady neurologic decline but also suffer superimposed attacks; and is the least common of all subtypes.

Treatments for MS include interferon β (Avonex, Betaseron, Rebif), Copaxone (Glatiramer acetate), and anti-VLA4 (Tysabri, natalizumab), which reduce relapse rate and to date have only exhibited a modest impact on disease progression. MS is also treated with immunosuppressive agents including methylprednisolone, other steroids, methotrexate, cladribine and cyclophosphamide. Many biological agents, such as anti-IFNgamma antibody, CTLA4-Ig (Abetacept), anti-CD20 (Rituxan), and other anti-cytokine agents are in clinical development for MS.

Peripheral neuropathies may also have a relapsing remitting course, and may include Miller Fisher syndrome; chronic inflammatory demyelinating polyneuropathy (CIDP) with its subtypes classical CIDP, CIDP with diabetes, CIDP/monoclonal gammopathy of undetermined significance (MGUS), sensory CIDP, multifocal motor neuropathy (MMN), multifocal acquired demyelinating sensory and motor neuropathy or Lewis-Sumner syndrome, multifocal acquired sensory and motor neuropathy, and distal acquired demyelinating sensory neuropathy; IgM monoclonal gammopathies with its subtypes Waldenstrom's macroglobulinemia, myelin-associated glycoprotein-associated gammopathy, polyneuropathy, organomegaly, endocrinopathy, M-protein, skin changes syndrome, mixed cryoglobulinemia, gait ataxia, late-onset polyneuropathy syndrome, and MGUS.

An inhibitory agent may inhibit the activity of CMKLR1 by a variety of different mechanisms. In certain embodiments, the inhibitory agent is one that binds to the protein CMKLR1 and, in doing so, inhibits its activity. In other embodiments, the inhibitory agent prevents expression or secretion of CMKLR1.

Representative CMKLR1 inhibitory agents include, but are not limited to: antisense oligonucleotides; antibodies; and the like. Other agents of interest include, but are not limited to: naturally occurring or synthetic small molecule compounds of interest, which include numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Such molecules may be identified, among other ways, by employing appropriate screening protocols.

The inhibitory agent may act on CMKLR1 mRNA to inhibit the activity of the target CMKLR1 by reducing the amount of CMKLR1 RNA present in the targeted cells, where the target cell may be present in vitro or in vivo. By "reducing the amount of" is meant that the level or quantity of the target CMKLR1 in the target cell is reduced by at least about 2-fold, usually by at least about 5-fold, e.g., 10-fold, 15-fold, 20-fold, 50-fold, 100-fold or more, as compared to a control, i.e., an identical target cell not treated according to the subject methods.

In another embodiment, the CMKLR1 inhibitor is an antibody. The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope. The term includes monoclonal antibodies, multispecific antibodies (antibodies that include more than one domain specificity), human antibody, humanized antibody, and antibody fragments with the desired biological activity.

Polyclonal antibodies can be raised by a standard protocol by injecting a production animal with an antigenic composition, formulated as described above. (See, e.g., Harlow and Lane, Antibodies: A Laboratory Manual, Cold Spring Harbor Laboratory, 1988.) In one such technique, a Class II target antigen comprising an antigenic portion of the polypeptide is initially injected into any of a wide variety of mammals (e.g., mice, rats, rabbits, sheep or goats). When utilizing an entire protein, or a larger section of the protein, antibodies may be raised by immunizing the production animal with the protein and a suitable adjuvant (e.g., incomplete Freund's, complete Freund's, oil-in-water emulsions, etc.) Alternatively, for monoclonal antibodies, hybridomas may be formed by isolating the stimulated immune cells, such as those from the spleen of the inoculated animal. These cells are then fused to immortalized cells, such as myeloma cells or transformed cells, which are capable of replicating indefinitely in cell culture, thereby producing an immortal, immunoglobulin-secreting cell line.

In addition, the antibodies or antigen binding fragments may be produced by genetic engineering. In this technique, as with the standard hybridoma procedure, antibody-producing cells are sensitized to the desired antigen or immunogen. The messenger RNA isolated from the immune spleen cells or hybridomas is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones, which co-express a heavy and light chain (resembling the Fab fragment or antigen binding fragment of an antibody molecule). The vectors that carry these genes are co-transfected into a host (e.g. bacteria, insect cells, mammalian cells, or other suitable protein production host cell). When antibody gene synthesis is induced in the transfected host, the heavy and light chain proteins self-assemble to produce active antibodies that can be detected by screening with the antigen or immunogen.

Antibodies with a reduced propensity to induce a violent or detrimental immune response in humans (such as anaphylactic shock), and which also exhibit a reduced propensity for priming an immune response which would prevent repeated dosage with the antibody therapeutic are preferred for use in the invention. Thus, humanized, single chain, chimeric, or human antibodies, which produce less of an immune response when administered to humans, are preferred for use in the present invention. Also included in the invention are multi-domain antibodies.

A chimeric antibody is a molecule in which different portions are derived from different animal species, for example those having a variable region derived from a murine mAb and a human immunoglobulin constant region. Techniques for the development of chimeric antibodies are described in the literature. See, for example, Morrison et al. (1984) *Proc. Natl. Acad. Sci.* 81:6851-6855; Neuberger et al. (1984) *Nature* 312:604-608; Takeda et al. (1985) *Nature* 314:452-454. Single chain antibodies are formed by linking the heavy and light chain fragments of the Fv region via an amino acid bridge, resulting in a single chain polypeptide. See, for example, Huston et al., Science 242:423-426; Proc. Natl. Acad. Sci. 85:5879-5883; and Ward et al. *Nature* 341:544-546.

Antibody fragments that recognize specific epitopes may be generated by techniques well known in the field. These fragments include, without limitation, F(ab')$_2$ fragments, which can be produced by pepsin digestion of the antibody molecule, and Fab fragments, which can be generated by reducing the disulfide bridges of the F(ab')$_2$ fragments.

Alternatively, single chain antibodies (Fv, as described below) can be produced from phage libraries containing human variable regions. See U.S. Pat. No. 6,174,708. Intrathecal administration of single-chain immunotoxin, LMB-7 [B3(Fv)-PE38], has been shown to cure of carcinomatous meningitis in a rat model. *Proc Natl. Acad. Sci. USA* 92, 2765-9, all of which are incorporated by reference fully herein.

In addition to entire immunoglobulins (or their recombinant counterparts), immunoglobulin fragments comprising the epitope binding site (e.g., Fab', F(ab')$_2$, or other fragments) are useful as antibody moieties in the present invention. Such antibody fragments may be generated from whole immunoglobulins by ficin, pepsin, papain, or other protease cleavage. "Fragment," or minimal immunoglobulins may be designed utilizing recombinant immunoglobulin techniques. For instance "Fv" immunoglobulins for use in the present invention may be produced by linking a variable light chain region to a variable heavy chain region via a peptide linker (e.g., poly-glycine or another sequence which does not form an alpha helix or beta sheet motif).

Candidate antibodies can be tested for by any suitable standard means, e.g. ELISA assays, etc. As a first screen, the antibodies may be tested for binding against the immunogen. After selective binding is established, the candidate antibody may be tested for appropriate activity in an in vivo model. In a preferred embodiment, antibody compounds may be screened using a variety of methods in vitro and in vivo. These methods include, but are not limited to, methods that measure binding affinity to a target, biodistribution of the compound within an animal or cell, or compound mediated cytotoxicity. These and other screening methods known in the art provide information on the ability of a compound to bind to, modulate, or otherwise interact with the specified target and are a measure of the compound's efficacy.

Anti-CMKLR1 antibodies may be administered daily, semi-weekly, weekly, semi-monthly, monthly, etc., at a dose of from about 0.01 mg, from about 0.1 mg, from about 1 mg, from about 5 mg, from about 10 mg, from about 100 mg or more per kilogram of body weight when administered systemically. Smaller doses may be utilized in localized administration, e.g. in direct administration to ocular nerves, etc. Humanized, chimeric human, or human antibodies are preferred for administering to human patients.

Methods of Screening for CMKLR1 Antagonists

Agents that can regulate demyelinating inflammatory disease in a subject can be identified by detecting the ability of an agent to antagonize the activity of CMKLR1. Antagonizing agents include, but are not limited to, agents that interfere with the interaction of CMKLR1 with its natural ligands, agents that reduce CMKLR1 expression (e.g., by reducing transcription or by inducing cell surface receptor desensitization, internalization and/or degradation), agents that reduce expression of endogenous ligands of CMKLR1, and agents that inhibit intracellular signals initiated by the binding of CMKLR1 with its ligands.

In certain embodiments, agents that can reduce demyelinating inflammatory disease in a subject can be identified by detecting the ability of an agent to interfere with (e.g., block) the interaction of CMKLR1 with its cognate ligand (e.g., chemerin). For example, a screening assay may be used that evaluates the ability of an agent to bind specifically to CMKLR1 (or its ligand) and prevent receptor:ligand interaction. Assays to determine affinity and specificity of binding are known in the art, including competitive and non-competitive assays. Assays of interest include ELISA, RIA, flow cytometry, etc. Binding assays may use purified or semi-purified protein, or alternatively may use primary cells or immortalized cell lines that express CMKLR1. In certain of these embodiments, the cells are transfected with an expression construct for CMKLR1. As an example of a binding assay, CMKLR1 is inserted into a membrane, e.g. whole cells, or membranes coating a substrate, e.g. microtiter plate, magnetic beads, etc. The candidate agent and soluble, labeled ligand (e.g., chemerin) are added to the cells, and the unbound components are then washed off. The ability of the agent to compete with the labeled ligand for receptor binding is determined by quantitation of bound, labeled ligand. Confirmation that the blocking agent does not cross-react with other chemoattractant receptors may be performed with a similar assay.

CMKLR1 protein sequences are used in screening of candidate compounds (including antibodies, peptides, lipids, small organic molecules, etc.) for the ability to bind to and modulate CMKLR1 activity. Agents that inhibit or reduce CMKLR1 activity are of interest as therapeutic agents for decreasing demyelinating inflammatory disease in a subject whereas agents that activate CMKLR1 activity are of interest as therapeutic agents for increasing demyelinating inflammatory disease in a subject. Such compound screening may be performed using an in vitro model, a genetically altered cell or animal, or purified protein corresponding to chemerin-like chemoattractant polypeptides or a fragment(s) thereof. One can identify ligands or substrates that bind to and modulate the action of the encoded polypeptide.

Polypeptides useful in screening include those encoded by the CMKLR1 gene, as well as nucleic acids that, by virtue of the degeneracy of the genetic code, are not identical in sequence to the disclosed nucleic acids, and variants thereof.

CMKLR1 ligands (e.g., chemerin or resolvin) are used in screening of candidate compounds (including antibodies, peptides, lipids, small organic molecules, etc.) for the ability to bind to and modulate the ligands ability to activate CMKLR1. Agents that inhibit or reduce the ability of a CMKLR1 ligand to activate CMKLR1 are of interest as therapeutic agents for decreasing demyelinating inflammatory disease in a subject whereas agents that increase the ability of a CMKLR1 ligand to activate CMKLR1 activity are of interest as therapeutic agents for increasing demyelinating inflammatory disease in a subject. Such compound screening may be performed using an in vitro model, a genetically altered cell or animal, or purified protein corresponding to chemerin-like chemoattractant polypeptides or a fragment(s) thereof. One can identify ligands or substrates that bind to and modulate the action of the encoded polypeptide.

Polypeptides useful in screening include those encoded by a CMKLR1 ligand gene (e.g., chemerin), as well as nucleic acids that, by virtue of the degeneracy of the genetic code, are not identical in sequence to the disclosed nucleic acids, and variants thereof.

Transgenic animals or cells derived therefrom are also used in compound screening. Transgenic animals may be made through homologous recombination, where the normal locus corresponding to chemerin-like chemoattractant is altered. Alternatively, a nucleic acid construct is randomly integrated into the genome. Vectors for stable integration include plasmids, retroviruses and other animal viruses, yeast artificial chromosomes (YACs), and the like. A series of small deletions and/or substitutions may be made in the coding sequence to determine the role of different exons in receptor binding, signal transduction, etc. Specific constructs of interest include antisense sequences that block expression of the targeted gene and expression of dominant negative mutations. A detectable marker, such as lac Z or GFP, may be introduced into the locus of interest, where up-regulation of expression will result in an easily detected change in phenotype. One may also provide for expression of the target gene or variants thereof in cells or tissues where it is not normally expressed or at abnormal times of development, for example by overexpressing in neural cells. By providing expression of the target protein in cells in which it is not normally produced, one can induce changes in cell behavior.

Compound screening identifies agents that modulate CMKLR1 activity or function. Of particular interest are screening assays for agents that have a low toxicity for normal human cells. A wide variety of assays may be used for this purpose, including labeled in vitro protein-protein binding assays, electrophoretic mobility shift assays, immunoassays for protein binding, and the like. Screening for the activity of G-protein coupled receptors (or GPCRs, of which CMKLR1 is a member) is well known in the art, and includes assays for measuring any of a number of detectible steps, including but not limited to: stimulation of GDP for GTP exchange on a G protein; alteration of adenylate cyclase activity; protein kinase C modulation; phosphatidylinositol breakdown (generating second messengers diacylglycerol, and inositol triphosphate); intracellular calcium flux; activation of MAP kinases; modulation of tyrosine kinases; modulation of gene or reporter gene activity, integrin activation, or chemotaxis inhibition. A detectable step in a signaling cascade is considered modulated if the measurable activity is altered by 10% or more above or below a baseline or control level. The baseline or control level can be the activity in the substantial absence of an activator (e.g., a ligand) or the activity in the presence of a known amount of an activator. The measurable activity can be measured directly, as in, for example, measurement of cAMP or diacylglycerol levels. Alternatively, the measurable activity can be measured indirectly, as in, for example, a reporter gene assay. Knowledge of the 3-dimensional structure of the encoded protein (e.g., CMKLR1 or a ligand, e.g. chemerin), derived from crystallization of purified recombinant protein, could lead to the rational design of small drugs that specifically inhibit activity. These drugs may be directed at specific domains and sites.

The term "agent" as used herein describes any molecule, e.g. protein or pharmaceutical, with the capability of modulating the physiological function of CMKLR1 or its ligand. Generally a plurality of assay mixtures are run in parallel with different agent concentrations to obtain a differential response to the various concentrations. Typically one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, lipids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Test agents can be obtained from libraries, such as natural product libraries or combinatorial libraries, for example.

Libraries of candidate compounds can also be prepared by rational design. (See generally, Cho et al., *Pac. Symp. Biocompat.* 305-16, 1998); Sun et al., *J. Comput. Aided Mol. Des.* 12:597-604, 1998); each incorporated herein by reference in their entirety). For example, libraries of phosphatase inhibitors can be prepared by syntheses of combinatorial chemical libraries (see generally DeWitt et al., *Proc. Nat. Acad. Sci. USA* 90:6909-13, 1993; International Patent Publication WO 94/08051; Baum, *Chem. & Eng. News,* 72:20-25, 1994; Burbaum et al., *Proc. Nat. Acad. Sci. USA* 92:6027-31, 1995; Baldwin et al., *J. Am. Chem. Soc.* 117:5588-89, 1995; Nestler et al., *J. Org. Chem.* 59:4723-24, 1994; Borehardt et al., *J. Am. Chem. Soc.* 116:373-74, 1994; Ohlmeyer et al., *Proc. Nat. Acad. Sci. USA* 90:10922-26, all of which are incorporated by reference herein in their entirety.)

A "combinatorial library" is a collection of compounds in which the compounds comprising the collection are composed of one or more types of subunits. Methods of making combinatorial libraries are known in the art, and include the following: U.S. Pat. Nos. 5,958,792; 5,807,683; 6,004,617; 6,077,954; which are incorporated by reference herein. The subunits can be selected from natural or unnatural moieties. The compounds of the combinatorial library differ in one or more ways with respect to the number, order, type or types of modifications made to one or more of the subunits comprising the compounds. Alternatively, a combinatorial library may refer to a collection of "core molecules" which vary as to the number, type or position of R groups they contain and/or the identity of molecules composing the core molecule. The collection of compounds is generated in a systematic way. Any method of systematically generating a collection of compounds differing from each other in one or more of the ways set forth above is a combinatorial library.

A combinatorial library can be synthesized on a solid support from one or more solid phase-bound resin starting materials. The library can contain five (5) or more, preferably ten (10) or more, organic molecules that are different from each other. Each of the different molecules is present in a detectable amount. The actual amounts of each different molecule needed so that its presence can be determined can vary due to the actual procedures used and can change as the technologies for isolation, detection and analysis advance. When the molecules are present in substantially equal molar amounts, an amount of 100 picomoles or more can be detected. Preferred libraries comprise substantially equal molar amounts of each desired reaction product and do not include relatively large or small amounts of any given molecules so that the presence of such molecules dominates or is completely suppressed in any assay.

Combinatorial libraries are generally prepared by derivatizing a starting compound onto a solid-phase support (such as a bead). In general, the solid support has a commercially available resin attached, such as a Rink or Merrifield Resin. After attachment of the starting compound, substituents are attached to the starting compound. Substituents are added to the starting compound, and can be varied by providing a mixture of reactants comprising the substituents. Examples of suitable substituents include, but are not limited to, hydrocarbon substituents, e.g. aliphatic, alicyclic substituents, aromatic, aliphatic and alicyclic-substituted aromatic nuclei, and the like, as well as cyclic substituents; substituted hydrocarbon substituents, that is, those substituents containing non-hydrocarbon radicals which do not alter the predominantly hydrocarbon substituent (e.g., halo (especially chloro and fluoro), alkoxy, mercapto, alkylmercapto, nitro, nitroso, sulfoxy, and the like); and hetero substituents, that is, substituents which, while having predominantly hydrocarbyl character, contain other than carbon atoms. Suitable heteroatoms include, for example, sulfur, oxygen, nitrogen, and such substituents as pyridyl, furanyl, thiophenyl, imidazolyl, and the like. Heteroatoms, and typically no more than one, can be present for each carbon atom in the hydrocarbon-based substituents. Alternatively, there can be no such radicals or heteroatoms in the hydrocarbon-based substituent and, therefore, the substituent can be purely hydrocarbon.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and anti-digoxin, etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The components are added in any order that provides for the requisite binding. Incubations are performed at any suitable temperature, typically between 4 and 400 C. Incubation periods are selected for optimum activity, but may also be optimized to facilitate rapid high-throughput screening. Typically between 0.1 and 3 hours will be sufficient.

Preliminary screens can be conducted by screening for compounds capable of binding to CMKLR1 or its ligand; compounds so identified are possible modulators. Compounds capable of binding to CMKLR1 are inhibitors if they do not activate the receptor and activators if they do. The binding assays usually involve contacting CMKLR1 or its ligand with one or more test compounds and allowing sufficient time for the protein and test compounds to form a binding complex. Any binding complexes formed can be detected using any of a number of established analytical techniques. Protein binding assays include, but are not limited to, methods that measure co-precipitation, co-migration on non-denaturing SDS-polyacrylamide gels, and co-migration on Western blots (see, e.g., Bennet, J. P. and Yamamura, H. I. (1985) "Neurotransmitter, Hormone or Drug Receptor Binding Methods," in *Neurotransmitter Receptor Binding* (Yamamura, H. I., et al., eds.), pp. 61-89.

Certain screening methods involve screening for a compound that modulates the expression of CMKLR1 or its ligand. Such methods generally involve conducting cell-based assays in which test compounds are contacted with one or more cells endogenously expressing CMKLR1 or its ligand and then detecting a modulation in expression (e.g., at the mRNA and/or protein level). In certain screening methods, a target cell has a reporter gene (e.g., GFP) under the control of the CMKLR1 promoter (or promoter of its ligand). The level of expression can be compared to a baseline value. The baseline value can be a value for a control sample or a statistical value that is representative of expression levels for a control population. Expression levels can also be determined for cells that do not express the CMKLR1 or its ligand, as a negative control. Such cells generally are otherwise substantially genetically the same as the test cells. Various controls can be conducted to ensure that an observed activity is authentic including running parallel reactions with cells that lack the reporter construct or by not contacting a cell harboring the reporter construct with test compound.

Certain screening methods involve screening for a compound that modulates gene expression normally regulated by CMKLR1 signaling. In certain embodiments, a cell-based assay is conducted in which a cell expressing CMKLR1 is contacted to a candidate agent (e.g., a CMKLR1 binding agent) and monitored for changes in gene expression that are similar, or substantially similar, to those induced by a natural ligand for CMKLR1. In certain other embodiments, a cell-based assay is conducted in which a cell expressing CMKLR1 is contacted to its natural ligand and a candidate agent and monitored for perturbations in gene expression. By "perturbations in gene expression", it is meant that the gene expression changes induced by a CMKLR1 ligand binding to CMKLR1 is altered when the candidate agent is present.

Certain screening methods involve screening for a compound that modulates CMKLR1 signaling events when contacted to a cell expressing CMKLR1. These assays can be carried out in the presence or absence of a natural ligand for CMKLR1. Such methods generally involve monitoring for modulation of downstream signaling events as described above, e.g., protein phosphorylation, GDP/GTP exchange, etc.

Compounds can also be further validated as described below.

Compounds that are initially identified by any of the foregoing screening methods can be further tested to validate their apparent activity. The basic format of such methods involves administering a lead compound identified during an initial screen to an animal that serves as a model for humans. The animal models utilized in validation studies generally are mammals. Specific examples of suitable animals include, but are not limited to, primates, mice, and rats.

Active test agents identified by the screening methods described herein that modulate CMKLR1 activity can serve as lead compounds for the synthesis of analog compounds. Typically, the analog compounds are synthesized to have an electronic configuration and a molecular conformation similar to that of the lead compound. Identification of analog compounds can be performed through use of techniques such as self-consistent field (SCF) analysis, configuration interaction (CI) analysis, and normal mode dynamics analysis. Computer programs for implementing these techniques are available. See, e.g., Rein et al., (1989) Computer-Assisted Modeling of Receptor-Ligand Interactions (Alan Liss, New York).

A functional assay that detects leukocyte chemotaxis may be used for confirmation. For example, a population of cells that demonstrate chemerin chemotaxis (e.g., dendritic cells or monocyte/macrophages) may be stimulated with chemerin and/or the candidate modulating agent. An agent that antagonizes CMKLR1 activity will cause a decrease in the locomotion of the cells in response to chemerin. An agent that potentiates CMKLR1 activity will act as a chemotaxis factor in the absence of chemerin and/or increase the chemotactic response induced by chemerin. Chemotaxis assays of that find use in these methods are known in the art, examples of which are described in U.S. patent application Ser. No. 10/958,527, entitled "Family of Cystatin-Related Chemoattractant Proteins" (incorporated herein by reference in its entirety). An agent that is a chemoattractant inhibitor will decrease the concentration of cells at a target site of higher concentration of chemerin.

EXPERIMENTAL

Example 1

The pathology of multiple sclerosis (MS) involves leukocyte extravasation of the blood-brain barrier and associated myelin damage, which leads to impaired nerve function and paralysis. Chemokines, adhesion molecules, and their receptors have been implicated in recruitment of inflammatory cells to the central nervous system (CNS) during MS. However, the mechanisms that regulate migration of various leukocyte subsets to the CNS remain poorly understood. Chemokine-like receptor (CMKLR)-1 (also known as ChemR23 or Dez) is a recently de-orphaned chemoattractant receptor that has emerging roles in macrophage migration during inflammatory processes. In this study, we examined the role of CMKLR1 in experimental autoimmune encephalomyelitis (EAE), a mouse model of human MS. We found that mice deficient in CMKLR1 are resistant to progressive EAE. CMKLR1-deficient mice had reduced inflammatory infiltrates in the brain and spinal cord, with especially marked differences in the CNS parenchyma. Together, the data demonstrate that CMKLR1 regulates autoimmune demyelinating disease; and CMKLR1 provides a target for blocking development of progressive EAE/MS.

Example 2

Mouse monoclonal antibody BZ186 specifically recognizes mouse serpentine protein CMKLR1. CMKLR1 possesses high homology with members of the chemoattractant receptor family, and binds the chemoattractant chemerin. CMKLR1 is selectively expressed in macrophages, natural killer (NK) cells, subsets of dendritic cells (DC), and adipocytes. Monoclonal antibodies directed against chemokine receptors are used to determine leukocyte expression profile of receptors during homeostasis or inflammation; role of various receptors in coordinating the immune response; role of various receptors in leukocyte development; identity of other proteins interacting with the chemokine receptor.

This mouse anti-mCMKLR1 antibody can be used in flow cytometry, as a blocking reagent in vitro and in vivo; and in immunocytochemistry and immunofluorescence. Monoclonal antibody BZ186 (isotype mIgG$_1$κ) was generated by immunizing a CMKLR1 KO mouse with wild-type total peritoneal exudate cells. mCMKLR1 is highly expressed on mouse macrophages, which make up ~30% of total peritoneal exudate cells. Splenocytes and draining lymph node cells were isolated from the immunized mouse and fused with SP2/0 myeloma cells. Hybridoma supernatants were screened for binding to the mCMKLR1/L1.2 cell line. Hybridomas secreting monoclonal antibodies specific for mCMKLR1 were isolated and cloned by limiting dilution. Anti-mCMKLR1 mAb BZ186 was purified from a large batch preparation of hybridoma supernatant. The antibody is composed of the constant region from mouse immunoglobulin heavy chain isotype G$_1$ and the constant region from the kappa light chain. The complementarity-determining regions (CDR) recognize mCMKLR1. mAb BZ186 was shown to stain peritoneal mouse macrophages by flow cytometry, and block mCMKLR1/L1.2 transfectant chemotaxis to chemerin in in vitro transwell migration assays. A modification is made by directly labeling the antibodies with a fluorophore for use in flow cytometry, eliminating the need for a second-stage reagent. The antibody can also be biotinylated, which allows for higher sensitivity in various assays. The mAb can be conjugated to magnetic microbeads, which can be used to separate and enrich/purify mCMKLR1+ cells.

Importantly, the BZ186 mAb blocks mCMKLR1 functional responses to chemerin.

In a variation of this method, a mouse is similarly immunized with human macrophages, and screened for specific binding to the human protein, preferably as presented on the cell surface, wherein a monoclonal antibody is obtained that blocks functional responses to human chemerin.

Example 3

Using the newly developed anti-mCMKLR1 mAb BZ186, we analyzed CMKLR1 expression on mouse spinal cord mononuclear cells by flow cytometry. Plasmacytoid dendritic cells, pDC, defined as $CD45^{hi}CD3^-CD19^-CD11b^-CD11c^{int}B220^+$, are CMKLR1-negative, whereas myeloid dendritic cells mDC, defined as $CD45^{hi}CD3^-CD19^-CD11b^+CD11c^{hi}B220^-$ and microglia, defined as $CD3^-CD19^-CD11b^+ CD45^{lo}$, isolated from the spinal cords of EAE mice are CMKLR1-positive.

Example 4

EAE is examined in CMKLR1 null mice immunized with MOG 35-55 in CFA. These mice are resistant to development of EAE relative to the wild-type. EAE is driven by pathogenic immune responses against myelin proteins and lipids. CMKLR1 may have an inflammatory role.

It is then determined whether treatment with agents that inhibit CMKLR1, including mAb BZ186 or RNAi specific for CMKLR1 or chemerin. To test this, WT mice with EAE are treated every two days with 10-100 µg of mAb BZ186 administered intravenously or intraperitoneally.

Methods

Mice. CMKLR1 null mice were developed by Deltagen. These null mice were generated from ES cells derived from the 129 mouse strain and backcrossed to the C57BL/6 background. The mice are viable and fertile, with no obvious prenatal defects.

EAE induction. EAE is induced in 8-12 week old female null and WT animals via subcutaneous immunization with 100 µg myelin oligodendrocyte glycoprotein) peptide, amino acids 35-55 (MOG 35-55) in an emulsion mixed (volume ratio 1:1) with Complete Freund's Adjuvant (containing 4 mg/ml of heat-killed *Mycobacterium tuberculosis* H37Ra). Mice are also injected intravenously with 250-400 ng of *Bordetella pertussis* toxin (BPT) in PBS at the time of, and two days following immunization. MOG 35-55 peptide is synthesized by the Stanford Protein and Nucleic Acid Facility and purified by high performance liquid chromatography (HPLC). Mice (n=8-10 per group) were examined daily for clinical signs of EAE and were scored as followed: 0=no clinical disease, 1=limp tail, 2=hindlimb weakness, 3=complete hindlimb paralysis, 4=hindlimb paralysis plus some forelimb paralysis, and 5=moribund or dead.

Histopathology. Brains and spinal cords are dissected from mice, fixed in 10% formalin in PBS and embedded in paraffin. Seven micron thick sections are stained with haematoxylin and eosin to detect inflammatory infiltrates and luxol fast blue for demyelination. Inflammatory lesions in brain, thoracic and lumbar spinal cord sections are counted by an examiner masked to the treatment status of the animal.

Treatment. WT mice are induced with EAE using MOG 35-55 and pertussis toxin. When mice have hindlimb weakness or paralysis, animals are divided into two groups balanced for mean clinical disease scores, and then injected intravenously or intraperitoneally every second day with saline, pH 7.0, or 10-100 µg monoclonal antibody diluted in saline.

Example 5

EAE is induced in animals as described above. In place of treatment with antibody, the animals are injected with cholesterol conjugated siRNA having the sequence Fw:CACCGGAAGATAACCTGCTTCAACACGAATGTTGAAGCAGGTTATCTTCC (SEQ ID NO. 1)

Fw:AAAAGGAAGATAACCTGCTTCAACATTCGTGTTGAAGCAGGTTATCTTCC (SEQ ID NO. 2)

or with an adenoviral siRNA construct, and the results are scored as described above.

Although the foregoing invention has been described in some detail byway of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

---

---

What is claimed is:

1. A method of decreasing demyelinating inflammatory disease in a subject, the method comprising:
   administering to said subject an effective amount of a chemokine-like receptor 1 (CMKLR1) antagonist, wherein said antagonist is an antibody or antigen binding fragment thereof that binds to CMKLR1.

2. The method of claim 1, wherein said antagonist inhibits ligand-induced signaling from CMKLR1 in a cell.

* * * * *

SEQUENCE LISTING

```
<160> NUMBER OF SEQ ID NOS: 2

<210> SEQ ID NO 1
<211> LENGTH: 50
<212> TYPE: DNA
<213> ORGANISM: Artificial Sequence
<220> FEATURE:
<223> OTHER INFORMATION: Conjugated polynucleotide

<400> SEQUENCE: 1
caccggaaga taacctgctt caacacgaat gttgaagcag gttatcttcc          50

<210> SEQ ID NO 2
<211> LENGTH: 50
<212> TYPE: DNA
<213> ORGANISM: Artificial Sequence
<220> FEATURE:
<223> OTHER INFORMATION: Conjugated polynucleotide

<400> SEQUENCE: 2
aaaaggaaga taacctgctt caacattcgt gttgaagcag gttatcttcc          50
```